United States Patent
Blum et al.

(10) Patent No.: US 7,563,412 B2
(45) Date of Patent: Jul. 21, 2009

(54) REACTOR FOR SOLID PHASE SYNTHESIS

(75) Inventors: Martin Blum, Edingen-Neckarhausen (DE); Gerald Zieres, Worms (DE)

(73) Assignee: Hoffmann-La Roche Inc., Nutley, NJ (US)

(*) Notice: Subject to any disclaimer, the term of this patent is extended or adjusted under 35 U.S.C. 154(b) by 398 days.

(21) Appl. No.: 10/580,993

(22) PCT Filed: Nov. 17, 2004

(86) PCT No.: PCT/EP2004/013007
§ 371 (c)(1),
(2), (4) Date: May 26, 2006

(87) PCT Pub. No.: WO2005/051515
PCT Pub. Date: Jun. 9, 2005

(65) Prior Publication Data
US 2007/0081922 A1    Apr. 12, 2007

(30) Foreign Application Priority Data
Nov. 26, 2003    (EP)    ................... 03104393

(51) Int. Cl.
*B01J 19/00*    (2006.01)
*B01D 24/00*    (2006.01)
*B01D 29/01*    (2006.01)
*B01D 29/39*    (2006.01)
*B01D 29/86*    (2006.01)
*F16K 31/44*    (2006.01)

(52) U.S. Cl. .............. 422/131; 422/129; 422/130; 210/220; 210/409; 210/411; 210/459; 210/321.72; 210/321.64; 210/321.77; 210/321.88; 251/82

(58) Field of Classification Search .............. 422/131, 422/129, 130; 530/334, 333; 96/7, 9, 11; 210/220, 409, 411, 459, 321.64, 321.72, 210/321.77, 321.88; 251/82
See application file for complete search history.

(56) References Cited

U.S. PATENT DOCUMENTS

| | | | | |
|---|---|---|---|---|
| 3,184,062 A | * | 5/1965 | Humbert, Jr. | 210/130 |
| 3,369,666 A | * | 2/1968 | Hultgren et al. | 210/130 |
| 3,567,023 A | * | 3/1971 | Buckman et al. | 210/130 |
| 3,666,097 A | * | 5/1972 | Ryan | 210/798 |
| 3,695,437 A | * | 10/1972 | Shaltis | 210/136 |
| 5,468,397 A | * | 11/1995 | Barboza et al. | 210/798 |
| 5,520,890 A | * | 5/1996 | Lorentzen et al. | 422/197 |
| 6,320,025 B1 | * | 11/2001 | Slavazza et al. | 530/334 |
| 6,974,539 B1 | * | 12/2005 | McKenzie | 210/136 |

* cited by examiner

*Primary Examiner*—Walter D Griffin
*Assistant Examiner*—Huy-Tram Nguyen
(74) *Attorney, Agent, or Firm*—George W. Johnston; Dennis P. Tramaloni (57) ABSTRACT

A Reactor (1) for solid phase synthesis comprises a vessel (2), a plurality of filters (3) arranged in the vessel (2) and a plurality of filtrate outlets (4) for evacuating the filtrate out of the filters (3). Each filter (3) is connected to one filtrate outlet (4). The reactor (1) comprises means (3, 4) for delivering a gas into the vessel (2) in a region of the vessel (2) near to the bottom (24) of the vessel (2) and beside the filters (3).

6 Claims, 6 Drawing Sheets

REACTOR FOR SOLID PHASE SYNTHESIS

The present invention relates to a reactor for solid phase synthesis.

Such reactors comprising a vessel with a filter are used for example for solid phase syntheses of peptides or other organic compounds. Solid phase syntheses are often conducted in reactors comprising filter elements, in particular filtering bottoms. For suspending the solid phase in a solution of reactants, these apparatuses can comprise an agitator. Usually big scale apparatuses are provided with such agitators. The common feature of all these apparatuses is a planar filter bottom for filtering the liquid phase after the synthesis and/or after a washing procedure. The apparatuses without agitators, which are typically used for laboratory applications, often mix the reactants and the solid phase by supplying a gas through the filter bottom.

A solid phase synthesis in such apparatuses proceeds for example as follows: After positioning the solid phase in the apparatus the solution of the reactants is added. The chemical reaction of the solution and the solid phase is now going on. During this reaction it is important that the solution is mixed well with the solid phase. After a certain time the liquid phase is removed out of the apparatus by filtering it through the filter bottom. The remaining solid phase is washed by the following washing procedure which is usually applied several times one after another: A washing medium is added to the remaining solid phase in the apparatus. The washing medium is acting on the solid phase while again it is important that the solid phase and the liquid phase (washing medium) are well mixed. After a certain time the washing medium is removed from the apparatus by filtering it through the filter bottom. The solid phase with a product, for example an intermediate product, built on itself remains in the apparatus ready for the next cycle-step of the synthesis to take place by adding a next solution of reactants and repeating the whole procedure. The procedure is repeated with solutions of same or different reactants until the desired product is built on the solid phase. At the end the product has only to be cleaved off of the solid phase.

During the filtration, which is applied in several steps of the above described procedure with an above described apparatus, a filter cake is built on the filter. The filtration time is dependent of the thickness of the filter cake and of the material of the solid phase. Especially in large scale procedures, e.g. procedures in a kg-scale up to a 100 kg-scale, with a substantial number of synthesis cycles, e.g. 15 which causes e.g. 135 filtering steps, the overall filtration time is limiting the efficiency of the whole synthesis. The thickness of the filter cake is dependent of the scale of the synthesis and the filtration time. It is growing with the scale in respect of the synthesis in a given apparatus and with advancing filtering time.

The material of the solid phase is another key factor for the filtration time. Materials causing a big filter resistance in the filter cake, e.g. fine-grained and/or compressible materials, have a negative impact on the synthesis procedure in respect of the filtration time. Therefore solid phase synthesis cannot be carried out in an economic manner using any solid phase. The filtering properties of the solid phase have also to be taken in account. A compressible solid phase or any solid phase causing a big filter resistance can cause uneconomic overall process times.

In apparatuses with an agitator the mechanical strain caused by agitating forces can partly destroy the solid phase. This destruction of the solid phase produces small fractions which have an impact on the filter resistance. The filter resistance is increasing and the filtration time is growing with increasing destruction of the solid phase. In some situations the filtration can be totally stopped since the solid phase is blocking the filter. Therefore, again solid phase synthesis cannot be carried out in an economic manner using any solid phase. The mechanical resistance to the forces produced by the agitator of the solid phase have also to be taken in account.

To solve the above described problems of solid phase syntheses in large scales, various continuous-flow apparatuses and procedures using centrifuges or columns have been developed. However, they are in general technically and/or procedurally complex and expensive.

In view of the disadvantages of the hitherto known, above described reactors for solid phase synthesis, the object of the invention is to provide a simple and inexpensive apparatus for economic large scale solid phase synthesis.

This object is achieved by a reactor for solid phase synthesis according to the invention as it is defined in the independent claim 1. Preferred embodiments can be gathered from the dependent claims.

The essence of the invention is the following: A reactor for solid phase synthesis comprises a vessel, a filter arranged in the vessel and a filtrate outlet for evacuating the filtrate out of the filter. The filter is connected to the filtrate outlet. The reactor comprises means for delivering a gas into the vessel in a region of the vessel near to the bottom of the vessel and beside the filter.

The gas, which can pass from the bottom to the top of the vessel, causes turbulences in a solution of reactants filled in the vessel and mixes the solution with the solid phase. For this reason, no agitator is necessary for a sufficient mixture in the vessel in order that an efficient synthesis is possible. In the reactor according to the invention the solid phase does not have to meet any requirements of filtering properties or mechanical resistance. If filters are used building filter cakes horizontally beside them, the gas loosens the filter cake of the filter and remixes the solid phase of the filter cake with the solution. By using such filters the filtering properties and the filtering time of the reactor can be hold constantly good. Suitable gases to be delivered to the vessel can be gases which react or which do not react with the solid phase and/or the other reactants, for example $N_2$, $O_2$, $O_3$, air, $SO_2$, chlorine or hydrogen chloride.

The filter of the reactor according the invention can comprise a filter cartridge, preferably a filter candle. Such filters are preferable embodiments of filters building filter cakes horizontally beside them as described above.

In a preferred embodiment of the invention the filter cartridge of the reactor comprises an intermediate bottom separating the filter cartridge in a lower chamber and an upper chamber. The lower chamber is connected to the filtrate outlet. The filter cartridge further comprises a one-way valve connecting the upper chamber with the lower chamber such that the intermediate bottom is pervious in direction from the upper chamber to the lower chamber but not in direction from the lower chamber to the upper chamber. With this kind of filters the gas can be delivered into the vessel via the lower chamber of the filter cartridge. Since it is not able to pass the intermediate bottom of the filter cartridge, it leaves the lower chamber through its sidewalls and enters the vessel automatically near to the bottom of the vessel and beside the filter.

The filtrate outlet can comprise a gas inlet for delivering the gas into the vessel through the lower chamber of the filter cartridge. This preferred embodiment of delivering the gas into the vessel allows to use the filtrate outlet also as a gas inlet. The function of the filtrate outlet can change alternating from outlet to inlet.

The vessel of a reactor according to the invention comprises preferably a plurality of filters. A plurality of smaller filters can have a bigger filtering surface than one bigger filter, so that the ratio between filtering surface and vessel bottom surface can be optimized. Furthermore, the thickness of the filter cake on a filter can be limited by using a plurality of filters to the half of the distance between adjacent filter.

The vessel of the reactor according to the invention advantageously comprises a double casing for temperature regulation. The double casing can comprise means for keeping the temperature in the vessel at a constant temperature optimized for the synthesis.

In a preferred embodiment of the invention the filter or filters comprise a slotted screen filter medium. Such a filter medium is a preferred strong medium successfully used in solid phase syntheses like for example in peptide synthesis.

The vessel can comprise a filtrate inlet connected to the filtrate outlet, such that the filtrate can return from the filtrate outlet via the filtrate inlet into the vessel. With such a vessel the solution can continuously circulate in the reactor. The solution can be recycled during the synthesis procedure. This is economically and ecologically advantageous for the overall procedure.

In a preferred embodiment of the invention the vessel comprises an exhaust connected to the means for delivering the gas such that the exhausted gas can return back into the vessel. In this way the gas can be almost completely recycled, which is economically and ecologically advantageous for the overall procedure.

The reactor can comprise a cascade of vessels each comprising an exhaust, which vessels are connected together in such a way that the exhaust of one vessel is connected to the means for delivering the gas of the following vessel. The gas can be recycled in a plurality of vessels and the efficiency of the gas increases, which is economically and ecologically advantageous for the overall procedure.

The reactor for solid phase synthesis according to the invention is described in more detail hereinbelow by way of exemplary embodiments and with reference to the attached drawings, in which.

Figure 1:
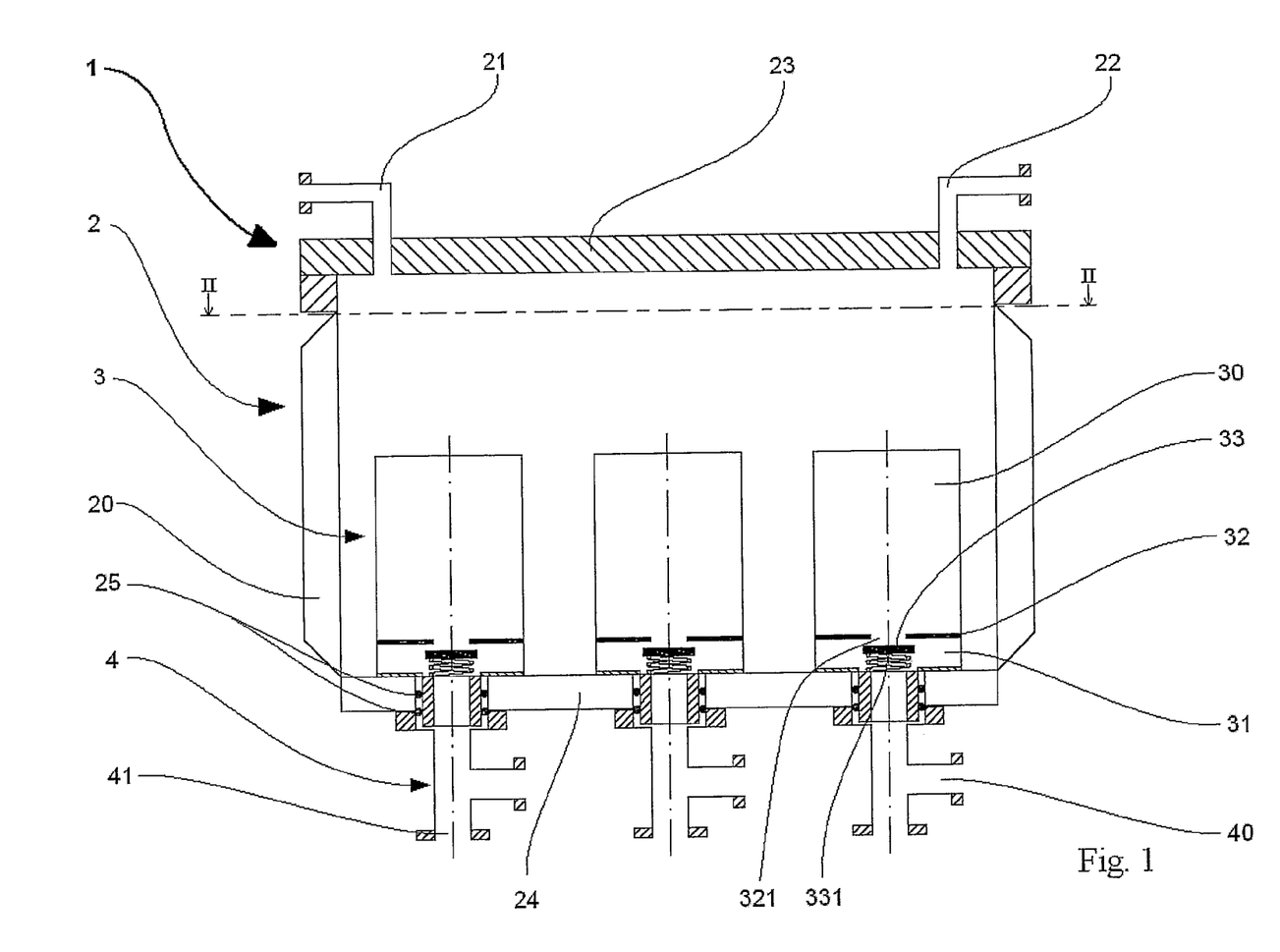
FIG. 1—shows a cross-sectional view of a first embodiment of a reactor according to the invention with a first embodiment of a vessel and a first embodiment of filter cartridges.

FIG. 1 shows a cross-sectional view of a first embodiment of a reactor 1 according to the invention with a first embodiment of a vessel 2 and a first embodiment of filters in form of filter cartridges 3. The vessel 2 comprises a removable cover 23, a tubular inlet 21 and a tubular outlet 22, which are both arranged at the cover 23 and through which a medium can be delivered into respectively removed out of the vessel 2. At its lateral sides the vessel 2 comprises a double casing 20. On the bottom 24 of the vessel 2 a plurality of filters is arranged, each filter comprising a vertically arranged filter candle 3 as a filter cartridge. In the present case, the filter candles 3 are fixed by a bayonet joint to the bottom 24, O-rings 25 being provided in the joint region for sealing. Each filter candle 3 comprises a cylindrical hollow body with filtering walls. The interior of the filter candle 3 is separated in an upper chamber 30 and a lower chamber 31 by an intermediate bottom 32. The intermediate bottom 32 has a centrally arranged opening 321 connecting the upper chamber 30 and the lower chamber 31. Below the opening 321 a spring-loaded back-pressure poppet valve 33 with a disk shaped valve head 331 is arranged at the bottom of the filter candle 3 as a one-way valve, such that the valve head 331 obturates the opening 321 in a normal state. Alternatively the spring-loaded back-pressure poppet valve 33 can be arranged on means for valve attachment, which are attached themselves at the intermediate bottom 32. During removal of the filtrate out of the filter candle 3 the valve head 331 is moved away from the opening 321, such that the intermediate bottom 32 is pervious in direction from the upper chamber 30 to the lower chamber 31. This situation is shown in FIG. 1. At the bottom of each filter candle 3 a tubular filtrate outlet 4 is connected to the lower chamber 31. The filtrate outlet 4 has a vertically arranged main tube 41 and a horizontally arranged gas inlet 40.

For a synthesis a dry solid phase or a solid phase suspended in a liquid can be delivered into the vessel 2 through the inlet 21. The solid phase is followed by a solution of reactants also delivered through the inlet 21 or through the gas inlet 40 and/or the main tube 41 into the vessel 2, such that the chemical reaction between the solution and the solid phase can start. The temperature in the vessel 2 can be optimized for the synthesis through a medium for heat exchange, which is conducted in the double casing 20 of the vessel 2. After a certain time the liquid phase (solution) can be removed out of the vessel 2. To effect this, the pressure conditions in the reactor 1 are changed, for example by closing the outlet 22 and delivering N2 into the vessel 2 via the inlet 21 to raise the pressure, such that the valve head 331 is moved away from the opening 321 and the liquid phase is conducted through the walls of the filter candles 3, the hollow interior of the filter candles 3 and the openings 321 into the filtrate outlets 4. The walls of the filter candles 3 are made of a filter medium, preferably a streamline filter medium, particularly a slotted screen filter medium. Like this the particles of the solid phase get caught by the walls and remain in the vessel 2. After the solution is removed out of the vessel 2 a washing medium can be delivered to the vessel 2 through the inlet 21 or through the gas inlet 40 and/or the main tube 41. After a certain time the liquid phase (washing medium) is removed out of the vessel 2 again through the filter candles 3. This washing process can be repeated several times. In a next step again a solution can be delivered into the vessel 2 through the inlet 21 or through the gas inlet 40 and/or the main tube 41 and the next cycle of the synthesis can start.

During the filtering steps of the synthesis a filter cake consisting of the solid phase of the synthesis is built on the walls of the filter candles 3. A gas is blown through the gas inlet 40 and the main tube 41 of the filtrate outlet 4 into the lower chamber of the filter candle 3 while the valve head 331 of the spring-loaded back-pressure poppet valve 33 obturates the opening 321 in the intermediate bottom 32. The gas streams out of all side-walls of the lower chamber 31 into the vessel 2, bubbles up the vessel 2, suspends the solid phase from the walls of the filter candles 3 and disperses the solid phase gathered at the filter candles 3 or settled at the bottom 24 of the vessel 2 by gravitation. Like this the solid phase can be mixed with the liquid phase in the vessel 2. The blowing of the gas into the vessel 2 advantageously happens intermittently to save gas. The gas itself can participate as a reactant in the synthesis, for example $O_2$, $O_3$, air, $SO_2$, chlorine or hydrogen chloride, or be inert, for example $N_2$. The remaining gas can leave the vessel 2 via the outlet 22, which acts in this case as an exhaust.

The following applies to the rest of this description. If, in order to clarify the drawings, a figure contains reference signs which are not explained in the directly associated part of the description, then it is referred to previous description parts.

Figure 2:
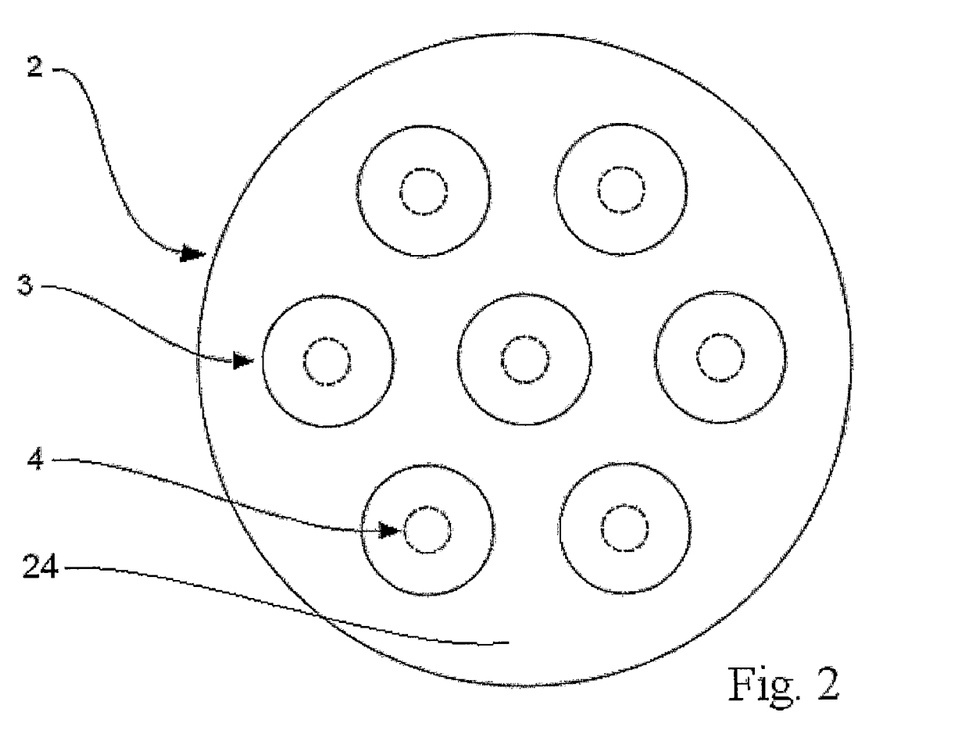
FIG. 2—shows a schematic sectional view of the reactor according to line II-II in FIG. 1.

FIG. 2 shows a schematic sectional view of the reactor 1 of FIG. 1. The vessel 2 has a circular outline and comprises seven filter candles 3 regularly arranged at the bottom 24 of the vessel 2. Each filter candle 3 is connected to a filtrate outlet 4. With a regular arrangement of filtering elements at the bottom 24 of the vessel 2 clearance volume can be prevented where the solid phase gathered at the filter candles 3 or settled at the bottom of the vessel 2 by gravitation cannot be sufficiently reached by the gas flow.

Figure 3:
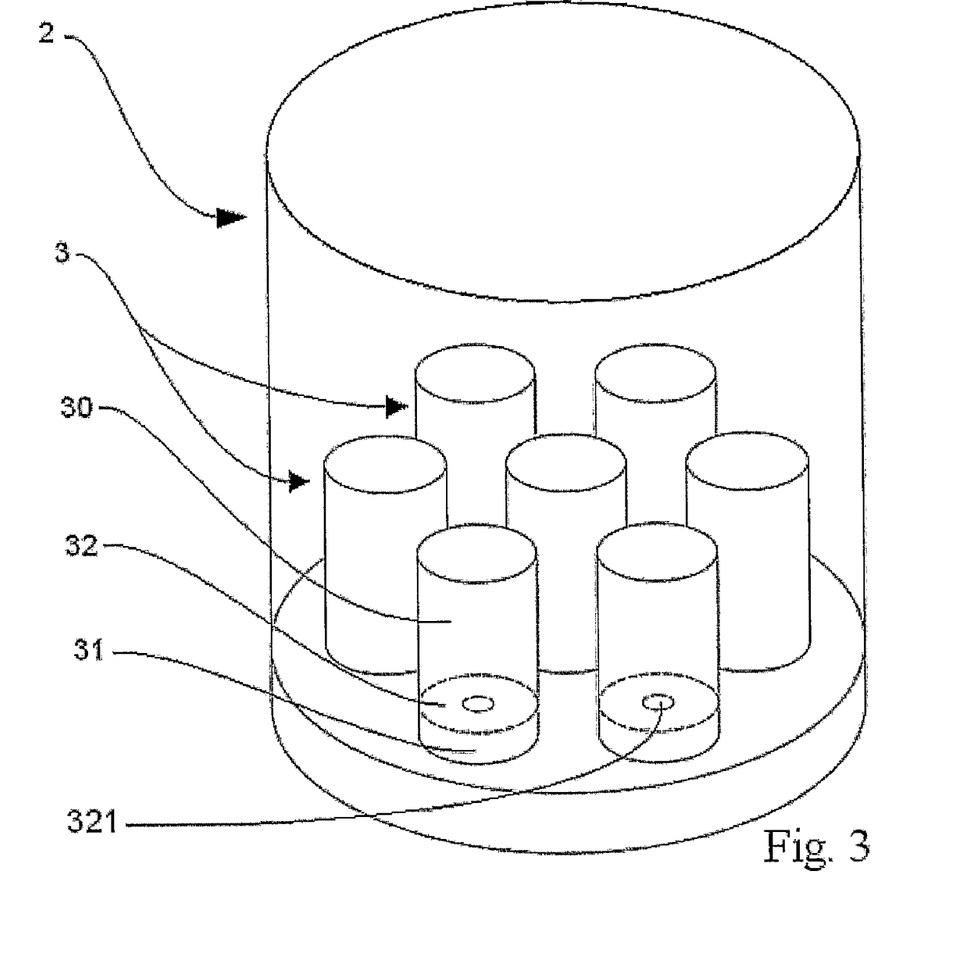
FIG. 3—shows a schematic perspective view of the reactor of FIG. 1.

FIG. 3 shows a schematic perspective view of the reactor of FIG. 1. The vessel 2 and the filter candles 3 are of a cylindrical shape with circular outline and with vertically arranged axes. Each filter candle 3 comprises a cylindrical upper chamber 30 arranged on top of a cylindrical lower chamber 31, separated by a intermediate bottom 32. The intermediate bottom 32 comprises a centrally arranged opening 321 under which a spring-loaded back-pressure poppet valve 33 is arranged.

Figure 4:
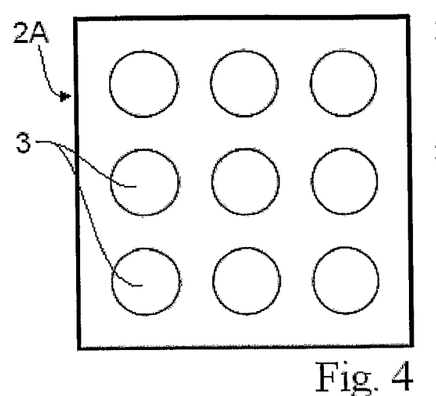
FIG. 4—shows a schematic sectional view of a second embodiment of a vessel with filter cartridges according to the first embodiment.

FIG. 4 shows a schematic sectional view of a second embodiment of a vessel 2A with the filter cartridges 3 according to the embodiment of FIG. 1. The vessel 2A has a square outline and comprises nine cylindrical filter candles 3 as described above.

Figure 5:
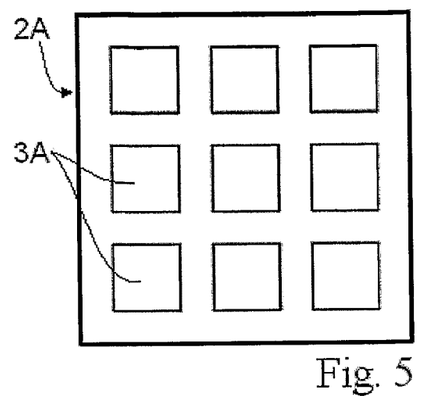
FIG. 5—shows a schematic sectional view of the vessel of FIG. 4 with a second embodiment of filter cartridges.
Figure 6:
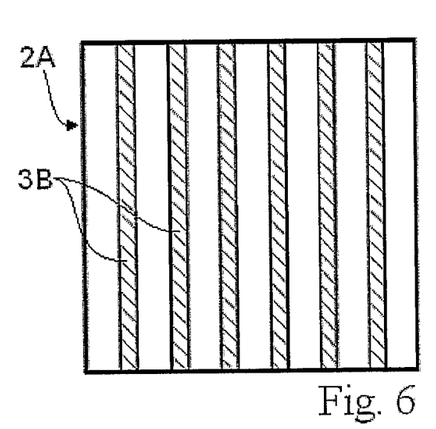
FIG. 6—shows a schematic sectional view of the vessel of FIG. 4 with a third embodiment of filter cartridges.
Figure 7:
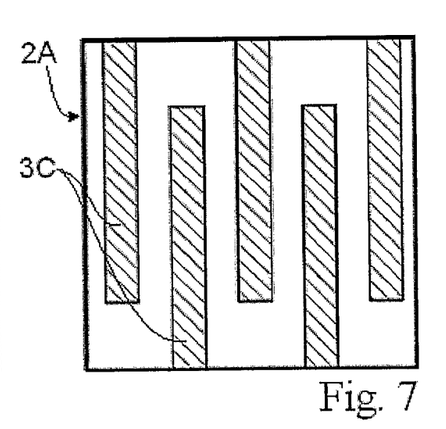
FIG. 7—shows a schematic sectional view of the vessel of FIG. 4 with a fourth embodiment of filter cartridges.

FIGS. 5, 6 and 7 show schematic sectional views of the vessel 2A of the embodiment of FIG. 4 but each with other embodiments of filter cartridges 3A, 3B, 3C. All embodiments of filter cartridges 3A, 3B, 3C are basically set up in the same manner as the filter candles 3 described above. They all are hollow and comprise an upper chamber 30 and a lower chamber 31 separated by an intermediate bottom 32. Each intermediate bottom 32 comprises an opening 321 under which a one-way valve 33 is arranged and which is connected to a filtrate outlet 4. These basic setups are not displayed in FIGS. 5, 6 and 7.

FIG. 5 shows filter candles 3A with square outlines. The square outlines of the filter candles 3A allow constant distances between the filter candles 3A and between the filter candles 3A and the walls of the vessel 2A. This allows a homogeneous synthesis especially in vessels 2A with square outlines.

FIG. 6 shows plate filter elements 3B as filter cartridges. The plate filter elements 3B are arranged in parallel end-to-end from one wall of the vessel 2A to an opposite wall of the vessel 2A.

FIG. 7 shows alternatively to FIG. 6 indented plate filter elements 3C. Several indented plate filter elements 3C are arranged in parallel starting right-angled to a first wall of the vessel 2A in direction of a second wall which is the opposite wall of the first wall. The indented plate filter elements 3C end before reaching the second wall. The adjacent indented plate filter elements 3C to the indented plate filter elements 3C starting at the first wall start at the second wall and end before reaching the first wall.

The filter medium used for the different embodiments of filter cartridges 3, 3A, 3B, 3C shown in FIGS. 4, 5, 6 and 7 can be chosen according to the requirements of the synthesis and the requirements of the construction of the reactor 1. It has on one hand to hold back the solid phase in the filtering steps of the synthesis procedure and on the other hand not to influence the synthesis reaction.

Figure 8:
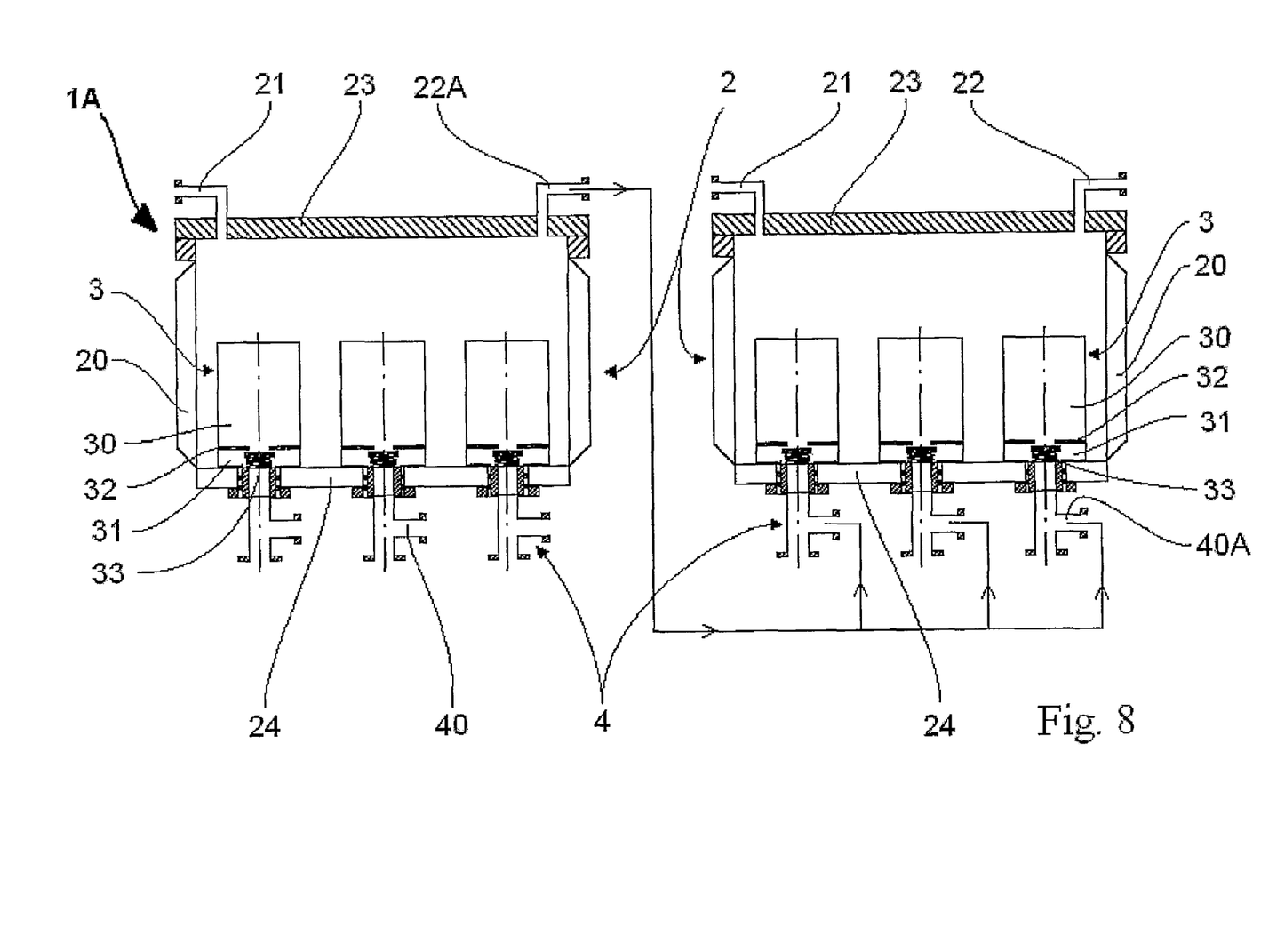
FIG. 8—shows a cross-sectional view of a second embodiment of a reactor according to the invention comprising two vessels.

FIG. 8 shows a cross-sectional view of a further embodiment of a reactor according to the invention. The reactor 1A comprises two vessels 2, which are similar to the vessel 2 shown in FIGS. 1, 2 and 3. The gas outlet or exhaust 22A of a first vessel 2 is connected to the gas inlets 40A of the filter candles 3 of the second vessel 2. The gas removed out of the first vessel 2 is delivered to the second vessel 2 and reused for dispersing the solid phase and as the case may be for reacting within the synthesis.

Figure 9:
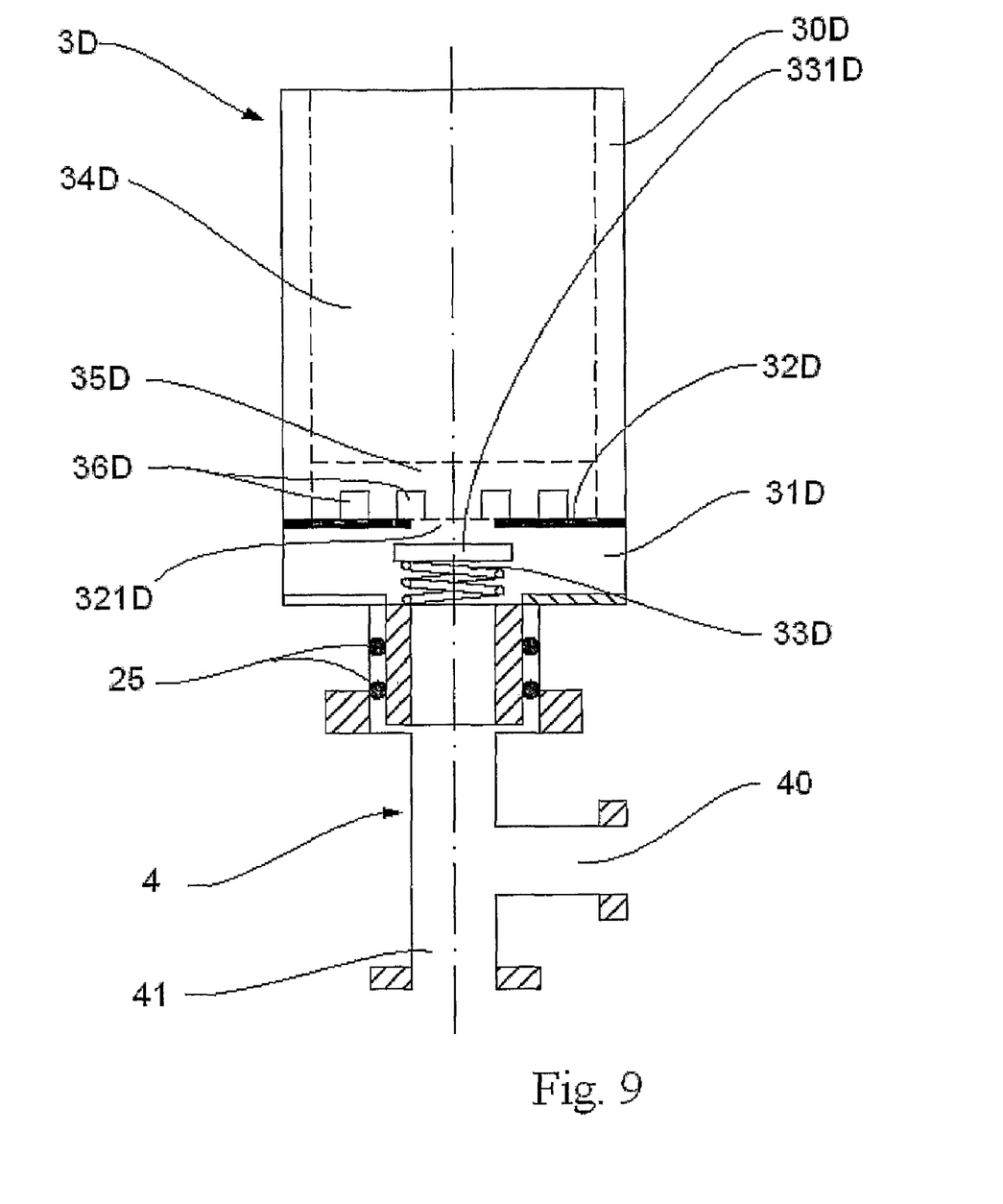
FIG. 9—shows a cross-sectional view of a fifth embodiment of a filter cartridge with a replacement body.

FIG. 9 shows a cross-sectional view of a filter candle 3D with a replacement body 34D as a fifth embodiment of a filter cartridge. The filter candle 3D is basically set up according to the filter candle described in FIG. 1. It comprises an upper chamber 30D and a lower chamber 31D separated by an intermediate bottom 32D. The intermediate bottom 32D has a centrally arranged opening 321D connecting the upper chamber 30D and the lower chamber 31D. Below the opening 321D a spring-loaded back-pressure poppet valve 33D with a disk shaped valve head 331D is arranged at the bottom of the filter candle 3D.

The cylindrical replacement body 34D is centrally arranged in the upper chamber 30D. It is impermeable for a liquid phase and comprises an upper part 34D and a lower part 35D. The lower part 35D is hollow and comprises a plurality of wall openings 36D.

During the use of the filter candle 3D, the liquid phase filtered through filtering walls of the filter candle 3D runs between the filtering walls and the replacement body 34D through the wall openings 36D into the inner of the lower part 35D. If the spring-loaded back-pressure poppet valve 33D is open the liquid phase runs into the lower chamber 31D of the filter candle 3D and in the filtrate outlet 4.

The replacement body 34D reduces the inner volume of the filter candle 3D accessible for a liquid phase filtered through filtering walls of the filter candle 3D. Since the inner volume of a filter candle without a replacement body 34D, as e.g. shown in FIG. 1, is not mixed, the overall unmixed volume of a reactor with filter candles 3D is significantly reduced.

Other alternative embodiments of the reactor according to the invention are realizable. Explicitly mentioned in this context are:

The exhaust of the vessel can be connected to the gas inlets of the filter candles of the same vessel to recycle the gas.

The filtrate outlet of the reactor is connected to the inlet in order that the reactor can be used as a continuous flow reactor. The liquid phase circulates in the reactor.

The body of the filter cartridge can basically be of any shape, like e.g. a filter candle with an oval outline or a filter candle with ring shaped outlines.

The gas can be delivered directly to the vessel without being delivered through the filtrate outlet and the filter cartridge by connecting the gas inlet with the bottom of the vessel. The one-way valve and the intermediate bottom in the filter cartridge are not needed in this embodiment. To guarantee a regular effect on the filter cake all around the filter cartridge there means can be provided to distribute the gas around the filter cartridge, for example a hollow ring arranged around a filter cartridge and comprising a gas inlet and a multitude of gas outlets or a gas outlet in form of a ring slot.

The reactor can comprise one filtrate outlet for a plurality of filters. For this purpose the filters can be connected together. For example the lower chambers can be connected in a way that the filtrate of a plurality of filters is gathered in one filtrate outlet.

The filters can be attached to the vessel in other ways than to its bottom with the help of bayonet joints and O-rings, for example with a snap in lock at the bottom, the sidewalls or the cover of the vessel or for example screwed in the bottom.

Instead of the slotted screen filter medium basic single-layer or multi-layer filter media can be used.

The invention claimed is:

1. A reactor for solid phase synthesis comprising vessel having a bottom, a filter arranged in the vessel and a filtrate outlet connected to the filter for evacuating a filtrate out of the filter, and means for delivering a gas into the vessel in a region of the vessel near the bottom of the vessel and beside the filter,
   wherein the filter comprises a filter cartridge, and
   wherein further the filter cartridge has an intermediate bottom that separates the filter cartridge into a lower chamber connected to the filtrate outlet and an upper chamber;
   and a one-way valve that connects the upper chamber with the lower chamber such that the intermediate bottom of the filter cartridge is pervious in the direction from the upper chamber to the lower chamber but not in the direction from the lower chamber to the upper chamber.

2. The reactor according to claim 1, wherein the filtrate outlet comprises a gas inlet for delivering the gas into the vessel through the lower chamber of the filter cartridge.

3. The reactor according to claim 1, wherein the vessel comprises a double casing for temperature regulation.

4. The reactor according to claim 1, wherein the vessel comprises a filtrate inlet connected to the filtrate outlet such that the filtrate can move from the filtrate outlet via the filtrate inlet into the vessel.

5. A reactor for solid phase synthesis comprising a vessel having a bottom, a filter arranged in the vessel and a filtrate outlet connected to the filter for evacuating a filtrate out of the filter, and means for delivering a gas into the vessel in a region of the vessel near the bottom of the vessel and beside the filter, wherein the vessel comprises an exhaust connected to the means for delivering the gas such that exhausted gas can return back into the vessel.

6. A reactor for solid phase synthesis comprising a vessel having a bottom, a filter arranged in the vessel and a filtrate outlet connected to the filter for evacuating a filtrate out of the filter, and means for delivering a gas into the vessel in a region of the vessel near the bottom of the vessel and beside the filter, further comprising a cascade of vessels each comprising an exhaust, wherein each vessel is connected together in such a way that the exhaust of one vessel is connected to the means for delivering the gas of the following vessel.

* * * * *